United States Patent [19]

Podolsky et al.

[11] Patent Number: 5,292,667
[45] Date of Patent: Mar. 8, 1994

[54] DETECTION AND TREATMENT OF ULCERATIVE COLITIS

[75] Inventors: Daniel K. Podolsky, Wellesley Hills; Deborah A. Fournier, Attleboro, both of Mass.

[73] Assignee: The General Hospital Corporation, Boston, Mass.

[21] Appl. No.: 678,574

[22] Filed: Mar. 20, 1991

Related U.S. Application Data

[63] Continuation-in-part of Ser. No. 213,222, Jun. 29, 1988, abandoned.

[51] Int. Cl.$^5$ .................. G01N 33/53; G01N 33/577; C07K 15/28; C12N 5/12
[52] U.S. Cl. ..................................... 436/548; 435/7.1; 435/240.27; 435/960; 436/63; 436/811; 530/388.2; 530/391.3; 530/836
[58] Field of Search .............. 436/548, 811; 435/7.92, 435/7.1, 7.2, 7.21, 7.93, 240.27; 530/350, 388.2, 391.3, 836

[56] References Cited

U.S. PATENT DOCUMENTS

| | | | |
|---|---|---|---|
| 4,444,744 | 4/1984 | Goldenberg | 424/1.1 |
| 4,650,756 | 3/1987 | Old et al. | 435/68 |
| 4,818,682 | 4/1989 | Linnane | 435/7.23 |

OTHER PUBLICATIONS

Podolsky et al., "Glycoprotein Composition of Colonic Mucosa", Gastroenterology 87:991 (1984).
Podolsky et al., "Composition of Human Colonic Mucin", J. Clin. Invest. 72:142 (1983).
Takahashi, "Isolation and Characterization of a Colonic Autoantigen Specifically Recognized by Colon Tissue-Bound Immunoglobulin G From Idiopathic Ulcerative Colitis", J. Clin. Invest. 76:311 (1985).
Vecchi et al., "Development of a Monoclonal Antibody Specifically Reactive to Gastrointestinal Goblet Goblet Cells", Proc. Natl. Acad. Sci. USA 84:3425 (1987).
Culling et al., "A Histochemical Comparison of the O-Acylated Sialic Acids of the Epithelial Mucins in Ulcerative Colitis, Crohn's Disease, and Normal Controls", J. Clin. Path. 32:1272 (1979).
Jacobs et al., "Regional Distribution and Alternations of Lectin Binding to Colorectal Mucin in Mucosal Biopsies from Controls and Subjects with Inflammatory Bowel Disease", J. Clin. Invest. 75:112 (1985).
Smith et al., "Biosynthesis and Secretion of Human Colonic Mucin Glycoproteins", J. Clin. Invest. 80:300, 1987.
Reid et al., "Chemical and Histochemical Studies of Normal/Diseased Human Gastrointestinal Tract, etc.", Histochemical J., 16:253 (1984).
Podolsky et al., "Development of Anti-Human Colonic Mucin Monoclonl Antibodies", 77:1251 (1986).
Podolsky et al., "Human Colonic Goblet Cells", J. Clin. Invest. 77:1263 (1986).
Boland et al., "Abnormal Goblet Cell Glycoconjugates in Rectal Biopsies Associated with an Increased Risk of Neoplasia in Patients, etc.", GUT 25:1364 (1984).
Koprowski et al., "Colorectal Carcinoma Antigens Detected by Hybridoma Antibodies", Somatic Cell Genetics 5:957 (1979).
Boland et al., "Glycoconjugates in the Colons of New World Monkeys with Spontaneous Colitis", Gastroenterology 92:625 (1987).
Podolsky et al., "Colonic Mucin Composition in Primates", Gastroenterology 88:20 (1985).
Podolsky et al., "Emergence of Antigenic Glycoprotein Structures in Ulcerative Colitis Detected Through Monoclonal Antibodies", Gastroenterology 95:371-378, (1988).
Das, et al., "The Production and Characterization of Monoclonal Antibodies to a Human Colonic Antigen Associated with Ulcerative Colitis: Cellular Localization of the Antigen . . . ", J. Immunology 139:77-84 (1987).
Panzini et al, Gastroenterology 94(5 Part 2) A341 (May 1988).

*Primary Examiner*—Esther L. Kepplinger
*Assistant Examiner*—Carol E. Bidwell
*Attorney, Agent, or Firm*—Fish & Richardson

[57] ABSTRACT

A monoclonal antibody which binds preferentially to colonic glycoproteins of cells of persons having ulcerative colitis, compared to colonic glycoproteins of cells of persons not having ulcerative colitis, and diagnostic and therapeutic uses thereof.

19 Claims, 1 Drawing Sheet

DETECTION AND TREATMENT OF ULCERATIVE COLITIS

This application is a continuation-in-part of Podolsky et al., U.S. Ser. No. 07/213,222, filed Jun. 29, 1988, now abandoned, herein incorporated by reference.

BACKGROUND OF THE INVENTION

This invention was made in part with the support of the Federal government, which has rights in the invention.

This invention relates to diagnosis and treatment of ulcerative colitis.

Ulcerative colitis is a recurrent acute inflammatory disease of the large intestine. Part or all of the large intestine may be involved, although the target of the pathogenic process is the colonic epithelium and primary tissue injury usually is confined to the colonic mucosa. Involvement may extend to the rectum, and infrequently crosses the ileocecal valve into the terminal ileum.

Typically the disease is progressive, characterized by episodes of exacerbation and remission. Generally the clinical course is more severe when the disease first appears early in the patient's life and when the early symptoms are severe. The prognosis is poorer when the extent of the involvement is greater, and is generally more favorable when only the sigmoid colon and the rectum are involved.

The etiology of ulcerative colitis is unknown. A number of studies have suggested that components of the immune system may mediate or contribute to injury observed in the colonic mucosa, but it remains unclear what initiates the pathogenic processes. It has been suggested that a primary abnormality of the immune system and its regulation might serve as primary initiating factors, or that the disease process might be initiated by an infectious agent and the injury then perpetuated through immune-mediated or other processes. Although the mucosal injury observed during episodes of acute disease can resemble the effects of any of a number of recognized infectious agents, no transmissible infectious agent has been consistently identified with ulcerative colitis. Alternatively, it has been suggested that aberrant structures in the colonic mucosa might increase susceptibility of the colonic mucosa to a lumenal factor, predisposing the colonic mucosa to injury by causing a defect in the mucosal barrier or initiating inappropriate activation of injurious immune-mediated processes.

Longstanding ulcerative colitis is generally recognized as a precancerous lesion, and a finite percentage of those affected with ulcerative colitis develop colonic adenocarcinoma, usually after a disease course of ten years or more.

Thus it can be desirable to be able to detect ulcerative colitis early in the patient's life, and to be able to distinguish ulcerative colitis from other intestinal inflammations, including other inflammatory diseases such as ischemic colitis and Crohn's disease and functional disorders such as irritable bowel syndrome. Early intervention can improve the long range prognosis for the patient having ulcerative colitis. Familial studies have suggested that a genetic factor may be involved in ulcerative colitis, and specific detection of the disease in prospective parents can be useful in genetic counseling.

A number of studies, including some employing specialized histochemical staining techniques, lectin probes, or direct characterization of glycoprotein heterogeneity in colonic mucosa, have suggested that glycoconjugates in the colonic mucosa are altered in patients having ulcerative colitis.

SUMMARY OF THE INVENTION

We have discovered that there exist "structural determinants" (i.e., antigenic determinants, or "epitopes") which can be present in tissues and tissue extracts from patients having ulcerative colitis, and which are absent from tissues and tissue extracts from clinically normal persons or from persons having inflammatory disease other than ulcerative colitis; and that monoclonal antibodies recognizing these "structural determinants" can be used in a highly specific assay for diagnosing ulcerative colitis.

In patients having active ulcerative colitis, samples of colonic mucosa taken from uninvolved regions of the colon can yield a positive diagnosis, so that accurate diagnosis can be accomplished even using a tissue sample taken from a site other than a site of involved tissue.

Moreover, samples of colonic mucosa from patients having ulcerative colitis but lacking active disease at the time of biopsy can yield a positive diagnosis, so that the tissue sample can be taken at a time other than during an episode of active inflammation.

The invention thus features a monoclonal antibody which binds preferentially to colonic glycoproteins of cells of persons having ulcerative colitis, compared to colonic glycoproteins of cells of persons not having ulcerative colitis (e.g., those who have other inflammatory diseases of the colon, such as Crohn's disease, or those who have colon cancer).

In preferred embodiments, the monoclonal antibody is coupled to a cytotoxic agent; the monoclonal antibody is labeled with a detectable label; the monoclonal antibody is radiolabeled or fluorescently labeled; the monoclonal antibody is produced by a hybridoma cell deposited in the American Type Culture Collection, Rockville, Md., on Jun. 22, 1988, and given ATCC Accession No. HB 9753; or by a hybridoma cell deposited in the American Type Culture Collection on Jun. 24, 1988, and given ATCC Accession No. HB 9756.

In another aspect, the invention features a hybridoma cell capable of producing a monoclonal antibody having the immunological identifying characteristics of (i.e., the same antigen-binding specificity as) the monoclonal antibody produced by the hybridoma cell given ATCC Accession No. HB 9753 or the monoclonal antibody produced by the hybridoma cell given ATCC Accession No. HB 756.

In preferred embodiments, the hybridoma cell is the hybridoma cell given ATCC Accession No. HB 9753 or the hybridoma cell given ATCC Accession No. HB 9756.

In another aspect the invention features a method for detecting the presence of ulcerative colitis in a human patient, which method includes contacting a colonic glycoprotein sample from the patient or a sample derived from the blood of the patient with a monoclonal antibody having the immunological identifying characteristics of the monoclonal antibody produced by the hybridoma cell given ATCC Accession No. HB 9753 or of the monoclonal antibody produced by the hybridoma cell given ATCC Accession No. HB 9756, and detecting immune complexes formed with the monoclonal antibody.

In another aspect, the invention features a method for detecting the presence of ulcerative colitis in a human patient, which method includes contacting a sample derived from the blood of the patient with ulcerative colitis-associated colonic glycoproteins and with a monoclonal antibody having the immunological identifying characteristics of the monoclonal antibody produced by the hybridoma cell given ATCC Accession No. HB 9753 or of the monoclonal antibody produced by the hybridoma cell given ATCC Accession No. HB 9756, and detecting immune complexes formed with the monoclonal antibody.

In another aspect the invention features a method for treating ulcerative colitis in a person, including administering to the patient in a pharmaceutically suitable carrier substance, a monoclonal antibody which binds preferentially to colonic glycoproteins of cells of persons having ulcerative colitis. Preferably, the monoclonal antibody to be administered in the pharmaceutically suitable carrier substance is coupled to a cytotoxic agent capable of killing the cells targeted by the monoclonal antibody.

Other features and advantages of the invention will be apparent from the following detailed description, and from the claims.

DETAILED DESCRIPTION

Figure 1:
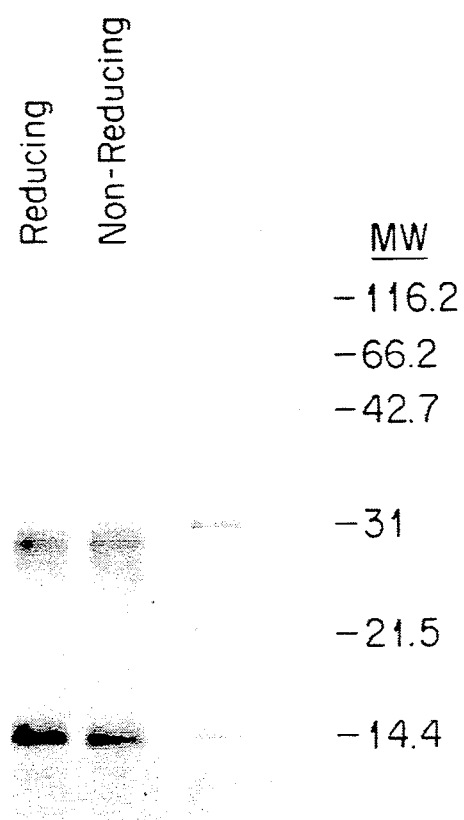

The drawing will first be described.

DRAWING

FIG. 1 is a Western blot analysis of ulcerative colitis-specific glycoproteins purified by immuno-affinity resin.

PREPARATION AND CHARACTERIZATION OF MONOCLONAL ANTIBODIES

Monoclonal antibodies ("MAbs") specific to "structural determinants" characteristic of colonic mucosa of humans having ulcerative colitis ("UC") are made using standard hybridoma techniques, following immunization of mammals, preferably mice, with mucin glycoproteins ("colonic mucin") isolated from colonic tissue from patients having UC. Supernatants from fusion products are screened in a solid phase differential binding assay using beads coated with mucin glycoproteins purified from samples of tissue from UC patients, normal subjects, and Crohn's disease patients.

By way of example, there follows a detailed description of the preparation, purification, and characterization of MAbs specific for structural determinants characteristic of UC colonic tissues, and, in particular, the preparation, purification, and characterization of two MAbs designated UC7 and UC11.

I. Isolation and purification of human colonic mucin.

Human colonic mucin (HCM) glycoproteins were prepared from mucosal scrapings of fresh surgical specimens of sigmoid and ascending colon from patients undergoing resection for chronic ulcerative colitis and Crohn's disease, as well as normal tissue from patients undergoing resection for diverticulosis or recurrent volvulus. Pure mucin glycoproteins were isolated from materials solubilized by sonication, using sequential Sepharose 4B column chromatography and CsCl density centrifugation generally as described in D.S. Podolsky et al., 1983, J. Clin. Invest., Vol. 72, pp. 142–153. Material was designated UC glycoproteins, normal glycoproteins, or CD glycoproteins reflecting the tissue source.

II. Preparation of anti-UC human colonic mucin monoclonal antibodies ("anti-UC HCM MAbs")

A. Immunization of mice.

Primary immunization of Balb/c mice (Charles River Breeding Laboratories, Wilmington, Ma.) was carried out with pure UC mucin glycoprotein (100 μg) by intravenous injection. Secondary and tertiary immunizations identical in route and amount were performed at subsequent 3–5 wk intervals. All animals received further doses of antigen on days 4 and 3 before fusion.

B. Fusion technique and production of monoclonal antibodies.

Splenocytes from immunized animals were prepared and fused with P2-NS1/1-Ag(NS1) myeloma cells as described, for example, in D.K. Podolsky et al., 1986, J. Clin. Invest., Vol. 77, pp. 125–1262. Hybrids were selected by use of medium containing hypoxanthine/aminopterin/thymidine ("HAT medium") on days 3, 4, and 5 after fusion. Surviving hybrids were transferred to 24-well culture plates (Costar, Cambridge, Ma.) and medium supernatants assessed for anti-UB mucin activity. Positive primary hybridomas were grown to confluence in Dulbecco's modified Eagle's medium supplemented with 20% fetal calf serum in 60-mm dishes, and assessed for activity against pooled UCHCM prepared from six separate specimens. Hybrids which bound UC HCM to a two-fold or greater extent than normal HCM were double-cloned at limiting dilution in complete medium of 3T3 monolayers previously treated with mitomycin c (1 μg/ml). After the second cloning cycle, larger amounts of MAbs were obtained by inoculating Balb/c mice intraperitoneally ($4 \times 10^6$ cells/animal) 1 wk after priming with pristane and subsequently collecting ascitic fluid.

C. Purification and characterization of MAbs

For isotypic analysis of anti-UC HCM MAbs, UC HCM-coated polystyrene beads were incubated first with medium supernatant from double-cloned anti-UC HCM hybridomas and then With $^{125}$I-labeled goat and anti-mouse IgG, IgG$_2$, IgA or IgM, and subsequently bound radioactivity was determined. Alternatively, isotype determinations were carried out using a commercially available peroxidase-linked immunoassay kit (Catalog No. 100–36; Boehringer Mannheim Diagnostics, Inc., Houston, Tex.).

IgM anti-UC HCM MAbs were purified from ascitic fluid by gel exclusion chromatography on Sepharose 4B, as described in Z.L. Jonak, et al., in *Monoclonal Antibodies*, RH Kennett, et al., eds. Plenum Press, New York, 1981, pp. 363–412. IgG MAbs were purified from ascitic fluid by chromatography on Staphylococcus A-Sepharose 4B (Pharmacia Fine Chemicals, Piscataway, N.J.), as described in P.C. Ey et al, 1978, Immunochemistry, Vol. 15, pp. 429–436. Purity of MAbs was assessed by sodium dodecyl sulfate polyacrylamide gel electrophoresis (SDS-PAGE), followed by staining with Coomassie Blue, as described in U.K. Laemmli, 1970, Nature (Lond.), Vol. 277, pp. 680–685.

Hybridomas were prepared as above from mice immunized with colonic mucin glycoproteins purified from mucosa of patients with ulcerative colitis. Among 1200 fusion products screened from five mice, 275 recognized the mixture of purified UC mucin glycoproteins when assessed in a solid phase binding assay. Parallel binding assays using beads coated with colonic glycoprotein prepared from normal colon demonstrated that the majority of hybridomas recognizing determinants in the UC tissue-derived material also bound to beads coated with glycoprotein derived from normal tissue. These findings indicate that the determinants recognized by 264 positive hybridomas (96%) were common to both normal and disease tissue. However, eleven hybridomas among the initial fusion products demonstrated preferential binding to UC-derived glycoproteins. These hybridomas, designated MAbs UC 1 through UC 11, were developed by subculturing at limiting dilutions through two cycles, and encompassed both IgM and IgG isotypes.

Although all of the initial fusion products from which these monoclonal cultures were derived bound UC HCM glycoproteins in a differential pattern relative to comparable material derived from normal tissue, several of the monoclonal antibodies showed only moderate selectivity when screened with beads coated with pooled preparations of colonic mucin glycoproteins. These findings suggest that the determinants recognized by these antibodies are not specifically related to ulcerative colitis or mucosal injury. The limited differential specificity of these monoclonal antibodies observed in the solid phase binding assay perhaps reflects differences in the relative or absolute amounts of the recognized structural epitopes. Among MAbs UC 1 through UC 11, only MAbs UC 7 and UC 11 retained pronounced (greater than 3-fold preference) differential binding to UC-derived glycoproteins, relative to pooled glycoproteins from normal colon.

D. Assay of anti-HCM activities

Anti-UC HCM and anti-normal HCM activities of culture supernatants and purified MAbs were assessed using solid phase sandwich radioimmunoassay (RIA). Polystyrene beads (0.25"; Precision Ball Co., Chicago, Ill.) were coated with purified HCM (50 μg of antigen/10 ml of PBS/40 beads) by incubation overnight at room temperature with gentle shaking. Approximately 5 ng of glycoproteins adhered to each bead, as determined by disappearance of hexose from the suspension buffer; the rate of adherence was similar for UC, normal and CD-derived preparations. Subsequent incubations were performed after placing beads in commercially available ELISA plates (10×20 reaction plates Comm. No. 93-8523 (Abbott Co; Chicago, Ill.) and washing steps were performed using an Abbott Pentawasher T apparatus according to the instructions of the manufacturer. Before use in binding assays, beads were incubated for 1 h in buffer containing either spent NS1 medium or 10% fetal calf serum to saturate sites of nonspecific binding. Coated beads were incubated with test sample at 37° C. for 60 min. After washing three times with water, the sandwich was completed by incubation with $^{125}$I-labeled sheep anti-mouse Ig Fab (100,000 cpm per well; specific activity, 7.3 μCi/mg; New England Nuclear, Boston, Ma.) in 150 μl of buffer containing 25% fetal calf serum, 0.01 M Tris-HCl (pH 8.5), EDTA at 2.0 mg/ml and thimerisol 50 μg/ml at 37° C. for 60 min. Bound radioactivity was measured after extensive washing with distilled water. Intra-assay variation was found to be limited to a SD±8% when individual samples were assayed in multiples (n=6). Samples were assayed in duplicate (variation<14%) and results were expressed as the mean value. Activity threefold greater than negative control (medium from NS1 cells or diluted serum from unimmunized animal) was considered positive. Statistical significance of differences in binding were determined by Student's t-test.

In some experiments, anti-UC HCM MAb binding activity was assessed using beads coated with a crude mixture of colonic mucosa-derived constituents. Colonic mucosal biopsies were sonicated after suspension in 10 ml phosphate buffered saline (PBS) containing penicillin/streptomycin and 2 mM phenylmethyl sulfonic fluoride, as described in Smith et al., 1987, J. Clin. Invest., Vol. 80, pp. 300-307. Soluble material obtained as the supernatant after centrifugation (105,000 xg, 60 min) was either used directly after adjustment of protein concentration or first dialyzed against water and lyophilized. The lyophilized material was used to coat polystyrene beads for binding assays as detailed above.

The specificity of MAbs UC 7 and UC 11 were examined in greater detail by assessing their binding to individual preparations of purified colonic mucin glycoproteins. MAb UC 7 demonstrated significantly more binding to 12 of 15 preparations of mucin glycoprotein derived from individual patients with ulcerative colitis when compared to 21 samples prepared from normal human colon. Binding to UC-derived glycoprotein resulted in mean bind of 10170±2740 cpm/~5 ng glycoprotein, compared to 2300±1080 cpm/~5 ng glycoprotein from normal tissue. The structural determinant recognized by MAb UC 7 does not appear to be related to mucosal injury in a nonspecific fashion. Binding of MAb UC 7 to mucin glycoproteins prepared from colonic mucosa of patients with Crohn's disease (with colonic involvement) was indistinguishable from normal controls. MAb UC 11 also bound UC-derived glycoprotein to a greater extent than normal and Crohn's disease colonic mucin glycoprotein when analyzed on beads coated with purified mucin glycoproteins in pooled preparations, and 9860 cpm UC vs. 1770 cpm normal for individual mucin glycoprotein samples.

E. Pinch biopsy specimen preparation and analysis of crude extracts

Pinch mucosal biopsy specimens were obtained from patients undergoing diagnostic flexible sigmoidoscopy or colonoscopy at Massachusetts General Hospital, Boston, Ma. Biopsy specimens were obtained at the same time that sampling was performed for routine histologic examination. Diagnostic classification of samples included in these studies was made on the basis of the examining physicians' reports and the official interpretation of diagnostic biopsy specimens by members of the Pathology Department at Massachusetts General Hospital. Additional samples were obtained from fresh surgical specimens. These studies were approved by the Human Studies Committee of Massachusetts General Hospital. All samples were promptly processed for immunofluorescent studies as described below.

The specificities of MAb UC 7 and MAb UC 11 were further explored through binding assays using crude mucosal extracts and IIF staining of colonic mucosal biopsies. MAb UC 7 was still able to recognize a determinant in crude extracts which was specifically associated with ulcerative colitis. The results of binding of MAb UC 7 to beads coated with the crude mixture of constituents solubilized from mucosal pinch biopsies was equivalent to that observed when purified mucin glucoproteins were used. Binding to material derived from normal tissue was also comparable to binding to Crohn's disease tissue, and approximately twice that found using beads coated with fetal calf serum (reflecting largely or entirely non-specific binding). MAb UC 7 did not bind significantly to constituents in tissue samples from several other colonic disorders which involve mucosal injury: experiments employing MAb UC 7 in the solid-phase binding assay described above utilized samples of colonic mucosa derived from 23 individuals diagnosed by standard methods as having ulcerative colitis and from 53 individuals with other bowel disorders, including 14 patients diagnosed as having functional bowel syndrome. Samples from the latter patients appear histologically normal and thus serve as the "normal" controls for purposes of this assay. The results are shown in Table 1.

TABLE 1

| Diagnosed Condition | Number of Patients | % Reacting with MAb UC 7 (cpm >3× Background) |
|---|---|---|
| Ulcerative Colitis | 23 | 87 |
| Crohn's Disease | 9 | 11 |
| Colon Cancer | 8 | 0 |
| Diverticulosis | 10 | 0 |
| Radiation Colitis | 3 | 0 |
| Ischemic Colitis | 2 | 0 |
| Infectious Colitis | 7 | 14 |
| Functional Bowel Syndrome ("Normal") | 14 | 0 |

While nearly all (20 out of 23) of the patients diagnosed by standard techniques as having ulcerative colitis produced glycoprotein samples that reacted with MAb UC 7, only two out of the 53 individuals diagnosed as having other bowel disorders (including functional bowel syndrome, the "normal" control) produced positively-reacting samples. This assay utilizing a monoclonal antibody of the invention thus serves as a useful means of distinguishing ulcerative colitis from other bowel disorders, including Crohn's disease, colon cancer, diverticulosis, radiation colitis, ischemic colitis, infectious colitis, and functional bowel syndrome.

In contrast to these results using MAb UC 7, it was not possible to demonstrate significant binding of MAb UC 11 to crude material solubilized from ulcerative colitis tissue or other samples, despite the observed binding to UC samples found when purified glycoproteins were used. The failure to observe binding of MAb UC 11 to the crude extract could reflect either the limited amount of the antigenic determinant specified by MAb UC 11 or the effect of other components in this complex mixture on the configuration and accessibility of the determinant.

F. Indirect immunofluorescence

Multiple frozen sections (~2 μm) were prepared from tissue specimens embedded in OCT compound (Miles Laboratories, Naperville, Ill.) for indirect immunofluorescent (IIF) staining as described in D.K. Podolsky DK, et al., 1986, J. Clin. Invest., Vol. 77, pp. 1263–1271. Sections were prefixed by sequential washing in cold ethanol (10 minutes), ethanol/acetone (1:1, v/v; 10 minutes) and acetone (20 minutes). After equilibration at room temperature, one drop of anti-UC HCM MAb-containing ascites, diluted 1:200 with phosphate buffered saline (PBS), or spent anti-UC HCM MAb culture medium supernatant was added to cover individual tissue sections, and slides were placed in a moist chamber at room temperature for 30 minutes. Control sections were incubated with ascites or media derived from the parent NS1 myeloma lines. Subsequently, ascites or medium was aspirated and sections were washed three times by immersion in excess PBS. After air drying, sections were stained by addition of fluorescein isothiocyanate (FITC)-conjugated rabbit antimouse Ig (Cappel Laboratories, Cochranville, Pa.) diluted 1:25 PBS. After incubation at room temperature for 30 minutes in a moist chamber, excess reagent was aspirated and sections were washed again as before; fluorescent staining was evaluated using a Zeiss fluorescence microscope.

Both MAb UC 7 and MAb UC 11 were found to stain colonic mucosa from patients with ulcerative colitis using indirect immunofluorescent staining techniques. However, these two antibodies stained mucosa in easily distinguishable patterns, consistent with the presumption that they recognize discrete structural determinants. MAb UC 11 appeared to recognize a determinant present on the colonocyte surface and within colonic goblet cells. While staining was found in colonic mucosal samples from several patients with ulcerative colitis, appreciable IIF staining was not invariable and was not observed in 4 of 10 biopsies. Staining appeared relatively specific, insofar as mucosal staining was observed in only four biopsies from normal and non-UC disease controls.

MAbs UC 7 also stained colonic mucosa in a distinctive fashion. MAb UC 7 stained structures on the apical surface of colonic epithelia in a discontinuous manner. In addition MAb UC 7 consistently stained cells present within the lamina propria (designated LPC) of biopsies from patients with ulcerative colitis. The cytoplasm and/or cell surface of these LPC were strongly stained by IIF techniques. Staining was not affected by prior incubation of tissue with mouse immunoglobulin, indicating that LPC staining was not related to non-specific adherence to Fc receptor-bearing cells. MAb UC 7 specifically stained mucosal biopsies from 8 of 10 patients with active UC and none of 10 normal controls or 11 disease controls, including 7 specimens from patients with Crohn's disease. MAb UC 7 also stained three of four samples of mucosa from uninvolved proximal regions of the colon in patients with left sided colitis and three of five samples from patients lacking acute disease activity.

III. Purification of a UC-specific glycoprotein from human colonic mucin.

Affinity resin was prepared using purified MAb UC 7 coupled to Affigel matrix material (Biorad) according to the manufacturer's directions. This affinity resin was contacted with a crude solubilized preparation of colonic glycoproteins from a patient with UC, and then washed thoroughly with PBS to remove unbound material. Glycoproteins which bound to the MAb UC 7 affinity resin were then eluted at high pH and analyzed by 10% SDS-PAGE. A Western blot of this gel (immunoblotted with MAb UC 7) reveals three bands (FIG. 1); similar results are obtained when the gel is silver stained. These results indicate that three species of glycoprotein bear UC-specific structural determinants recognized by MAb UC 7, and that the affinity resin procedure described is capable of substantially purifying from a crude mixture those UC-specific glycoproteins recognized by MAb UC 7.

AVAILABILITY OF MABS AND HYBRIDOMAS

Hybridoma lines producing Mabs UC 7 and UC 11 were deposited in the American Type Culture Collection, Rockville, Md., and assigned ATCC Accession Nos. 9753 and 9756, respectively. These deposits were made on Jun. 22, 1988 (UC 7) and Jun. 24, 1988 (UC 11). Applicants' assignee, the General Hospital Corporation, agrees that upon allowance and issuance of the above-named application as a United States Patent, all restrictions on the availability of the deposits designated in this application will be irrevocably removed, and until such issuance, the deposits will be made available to the Commissioner of Patents under the terms of 37 C.F.R. §1.14 and 35 U.S.C. §122. The assignee further agrees that the designated cultures will be maintained in the ATCC throughout the effective life of a patent granted, for 30 years from the date of deposit, or for 5 years after the last request for the deposit after issuance of the patent, whichever is the longer, and that the deposits will be replaced if they should ever mutate or become inviable.

USE

The MAbs of the invention can be used in both diagnostic and therapeutic applications.

DIAGNOSIS

A patient suspected of having UC is tested, using the MAbs of the invention, according to standard immunoassay techniques, generally as follows. First, a sample is obtained from the patient. This sample can be a colonic mucosa sample obtained by pinch biopsy, or it can be a mucin sample or a sample obtained by a scraping of the colonic mucosa. The sample need not be obtained from the site of suspected active disease, but can be obtained from any region of the patient's colon. The sample is contacted with an MAb of the invention such that glycoproteins present in the sample are permitted to come in contact with the MAb so that, if the sample contains a UC-associated glycoprotein recognized by the MAb, the glycoprotein and MAb will form detectable immune complexes. Any standard immunoassay procedure can be used, e.g., where sample glycoprotein is solubilized or otherwise liquified prior to assay, an ELISA can be used, in which UC glycoproteins are sandwiched between an immobilized MAb and an enzyme-labeled MAb. Other labels can be used as well, e.g., fluorophores, heavy metals, and radioisotopes. Where glycoprotein solubilization is not carried out prior to assay, tissue analysis is carried out using a conventional immuno-staining technique.

The MAbs of the invention can be used according to standard immunoassay techniques to test for the presence of UC-associated antigens in the blood of a patient suspected of having UC. A blood sample or a sample of serum derived from blood of the patient can be contacted with an MAb of the invention such that antigens present in the sample are permitted to come in contact with the MAb so that, if the sample contains an antigen recognized by the MAb, the antigen and the MAb will form detectable immune complexes. A measure of the detectable immune complexes can provide a measure of the antigen. Also, the MAbs of the invention can be used to test for the presence of antibodies to UC-associated antigens in the blood of a patient suspected of having UC. For example, a sample of blood or serum from the patient can be contacted with UC glycoproteins such that antibodies present in the serum are permitted to come in contact with the UC glycoproteins so that, if the sample contains an antibody that recognizes the UC glycoprotein, the antibody will form immune complexes with the added UC glycoproteins. A measure of inhibition by the serum sample of binding of an MAb of the invention to the serum-contacted UC glycoproteins can provide a measure of the antibody in the sample.

The MAbs of the invention can also be used to locate regions of a patient's colonic mucosa which may be at risk for developing ulcerative lesions. The MAbs are labeled, preferably with radioactive, fluorescent, or heavy metal labels, and then used in a standard in vivo immuno-staining method; labeled regions of the colon are those containing cells in which there are glycoproteins characteristic of UC.

TREATMENT

One hypothesis is that the colonic mucosal cells which produce glycoproteins characteristic of UC are not only diagnostic for the UC, but are causative agent of the disease, e.g., the cells participate in the formation of ulcerative lesions. If this hypothesis is correct, the MAbs of the invention could be used to destroy those cells and thus treat the disease. Antibody is admixed with a pharmaceutically-acceptable carrier substance, e.g., saline, in a concentration of between about 0.5 µg antibody/ml and 500 µg antibody/ml. Antibody is administered using any appropriate procedure, e.g., intravenous administration. The amount of antibody administered in a single administration will generally be in the range of about 50 µg to 500 µg; multiple administrations will probably be required. If the antibody employed therapeutically is a lytic antibody (i.e., an IgG antibody), it may be capable of destroying unwanted UC-associated cells by itself, in the presence of endogenous complement. For non-lytic antibodies, and probably for lytic antibodies as well, enhanced cell destruction can be achieved by chemically linking, by conventional methods, the antibody to a cytotoxic agent, which is selectively delivered to the unwanted cells by the targeting antibody. Such cytotoxic agents include natural toxins such as ricin and diphtheria toxin, as well as cytotoxic radioactive agents.

Other embodiments are within the following claims.

What is claimed is:

1. A monoclonal antibody produced by a hybridoma selected from the group consisting of ATCC Accession HB 9753 and HB 9756.

2. The monoclonal antibody of claim 1, wherein said monoclonal antibody is labeled with a detectable label.

3. The monoclonal antibody of claim 2, wherein said monoclonal antibody is radiolabeled.

4. The monoclonal antibody of claim 2, wherein said monoclonal antibody is fluorescently labeled.

5. A monoclonal antibody which specifically binds to the same epitope as the monoclonal antibody produced by the hybridoma having ATCC Accession No. HB 9753.

6. A monoclonal antibody which specifically binds to the same epitope as the monoclonal antibody produced by the hybridoma having ATCC Accession No. HB 9756.

7. The monoclonal antibody produced by the hybridoma given the ATCC Accession No. HB 9753.

8. The monoclonal antibody produced by the hybridoma given the ATCC Accession No. HB 9756.

9. A hybridoma which produces a monoclonal antibody which specifically binds to the same epitope as the monoclonal antibody produced by the hybridoma given the ATCC Accession No. HB 9753.

10. A hybridoma which produces a monoclonal antibody which specifically binds to the same epitope as the monoclonal antibody produced by the hybridoma given the ATCC Accession No. HB 9756.

11. The hybridoma given the ATCC Accession No. HB 9753.

12. The hybridoma given the ATCC Accession No. HB 9756.

13. A method for detecting the presence of colonic mucin glycoprotein associated with ulcerative colitis in a human patient, comprising contacting a sample suspected of containing said glycoprotein from said patient with a monoclonal antibody of claim 5, and detecting immune complexes formed with said monoclonal antibody, wherein the presence of said complexes indicates the presence of said colonic mucin glycoprotein associated with ulcerative colitis.

14. A method for detecting the presence of colonic mucin glycoprotein associated with ulcerative colitis in a human patient, comprising contacting a sample suspected of containing said glycoprotein from said patient with a monoclonal antibody of claim 6 and detecting immune complexes formed with said monoclonal antibody, wherein the presence of said complexes indicates the presence of said colonic mucin glycoprotein associated with ulcerative colitis.

15. A method to aid in the diagnosis of ulcerative colitis in a human patient, comprising contacting a sample suspected of containing ulcerative colitis mucin glycoprotein, said sample being derived from blood of said patient, with a monoclonal antibody of claim 5, and detecting immune complexes formed with said monoclonal antibody, wherein the presence of said complexes is an indication that said patient has ulcerative colitis.

16. A method to aid in the diagnosis of ulcerative colitis in a human patient, comprising contacting a sample suspected of containing ulcerative colitis mucin glycoprotein, said sample being derived from blood of said patient, with a monoclonal antibody of claim 6, and detecting immune complexes formed with said monoclonal antibody, wherein the presence of said complexes is an indication that said patient has ulcerative colitis.

17. A hybridoma which produces the monoclonal antibody of claim 1.

18. A method to aid in the diagnosis of ulcerative colitis in a human patient, comprising contacting a sample suspected of containing colonic mucin glycoprotein associated with ulcerative colitis from said patient with a monoclonal antibody of claim 1, and detecting immune complexes formed with said monoclonal antibody, wherein the presence of said complexes is an indication that said patient has ulcerative colitis.

19. A method to aid in the diagnosis of ulcerative colitis in a human patient, comprising contacting a sample derived from the blood of said patient, said sample suspected of containing ulcerative colitis-associated mucin glycoprotein, with a monoclonal antibody of claim 1, and detecting immune complexes formed with said monoclonal antibody, wherein the presence of said complexes is an indication that said patient has ulcerative colitis.

* * * * *

UNITED STATES PATENT AND TRADEMARK OFFICE
CERTIFICATE OF CORRECTION

PATENT NO. : 5,292,667
DATED : March 8, 1994
INVENTOR(S) : Daniel K. Podolsky et al It is certified that error appears in the above-indentified patent and that said Letters Patent is hereby corrected as shown below:

Column 2, line 54, replace "HB 756" with --HB 9756--.
Column 11, claim 14, line 23, delete "mucin".

Signed and Sealed this

Twelfth Day of July, 1994

Attest:

BRUCE LEHMAN

Attesting Officer        Commissioner of Patents and Trademarks